United States Patent [19]

White

[11] 4,022,764

[45] May 10, 1977

[54] 3-(META-OXYPHENYL) HEXAHYDROAZEPINES

[75] Inventor: Alan Chapman White, Windsor, England

[73] Assignee: John Wyeth & Brother Limited, Maidenhead, England

[22] Filed: Jan. 27, 1975

[21] Appl. No.: 544,477

[30] Foreign Application Priority Data

Feb. 4, 1974 United Kingdom ............ 04949/74

[52] U.S. Cl. ................... 260/239 B; 260/239 BF; 424/244

[51] Int. Cl.² ...................................... C07D 223/04

[58] Field of Search .................. 260/239 B, 239 BF

[56] References Cited

UNITED STATES PATENTS 3,729,465   4/1973   Cavalla .......................... 260/239 B Primary Examiner—Donald G. Daus
Assistant Examiner—Mark L. Berch

[57] ABSTRACT

The invention concerns novel hexahydroazepines of the formula

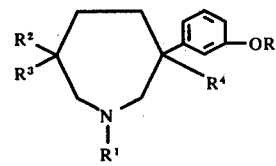

and their pharmaceutically acceptable acid addition salts, wherein R is hydrogen, lower alkyl, benzyl or lower alkanoyl, $R^1$ is hydrogen, lower alkyl, lower alkenyl, lower alkynyl, benzyl or cyclopropylmethyl, $R^2$ is hydrogen, lower alkyl, lower alkenyl or lower alkynyl, $R^3$ is lower alkyl, lower alkenyl or lower alkynyl and $R^4$ is lower alkyl. The compounds are useful as analgesic agents.

5 Claims, No Drawings

3-(META-OXYPHENYL) HEXAHYDROAZEPINES

This invention relates to novel hexahydroazepines, to processes for their preparation and to pharmaceutical compositions containing certain of them.

The novel hexahydroazepines provided by the present invention are compounds of the general formula (I)

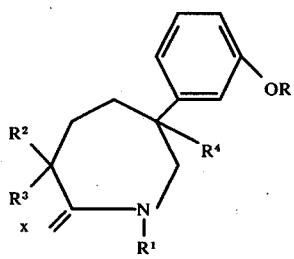

and their acid addition salts, wherein X represents oxo or two hydrogen atoms, R is hydrogen, lower alkyl, benzyl or lower alkanoyl, $R^1$ is hydrogen, lower alkyl, lower alkenyl, lower alkynyl, benzyl or cyclopropyl-methyl, $R^2$ is hydrogen, lower alkyl, lower alkenyl or lower alkynyl, $R^3$ is lower alkyl, lower alkenyl or lower alkynyl and $R^4$ is lower alkyl.

The term "lower" whenever applied to a radical in this specification means that the radical contains up to 6 carbon atoms. Preferably, the radical contains up to 4 carbon atoms.

Particularly important compounds of the invention are those of general formula (II)

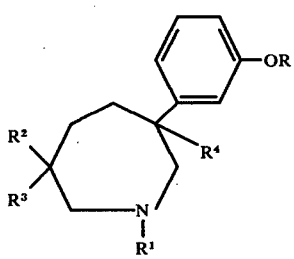

and their pharmaceutically acceptable acid addition salts. In formula (II), R, $R^1$, $R^2$, $R^3$ and $R^4$ have the meanings given above. The compounds of general formula (II) and their pharmaceutically acceptable acid addition salts are particularly important because they possess analgesic activity.

The compounds of general formula (I) in which X represents oxo, i.e. the hexahydro-2H-azepin-2-ones of general formula (III)

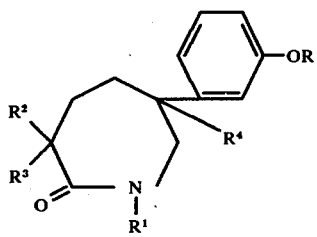

wherein R, $R^1$, $R^2$, $R^3$ and $R^4$ have the meanings given above), and their acid addition salts are useful as intermediates for preparing the pharmacologically active compounds of general formula (II).

In the compounds of general formula (I) R can represent hydrogen, lower alkyl (such as methyl, ethyl, propyl or butyl), benzyl or lower alkanoyl (such as acetyl). Particularly preferred meanings of R are hydrogen and methyl. The group $R^1$ can represent hydrogen, lower alkyl (such as methyl, ethyl, propyl or butyl), lower alkenyl (e.g. allyl, 2-methyl-2-propenyl, 3-methylbut-2-enyl), lower alkynyl (e.g. propynyl), benzyl and cyclopropylmethyl. Preferably $R^1$ is a lower alkyl group. $R^3$ can be lower alkyl (e.g. methyl, ethyl, propyl, butyl), lower alkenyl (e.g. vinyl, allyl) or lower alkynyl (e.g. ethynyl, propynyl). $R^2$ can have a similar meaning or can be hydrogen. Preferably $R^3$ has the same meaning as $R^1$ (e.g. lower alkyl such as methyl) and $R^2$ is also the same or represents hydrogen. $R^4$ is a lower alkyl group (e.g. methyl, ethyl, n-propyl, iso-propyl, neopentyl).

The novel compounds of general formula (II) can be prepared by reduction of the hexahydro-2H-azepin-2-ones of general formula (III). The hexahydro-2-H-azepin-2-ones can be reduced with, for example, a hydride transfer agent (e.g. lithium aluminium hydride).

Once a compound of general formula (II) has been prepared it may be converted into another compound of general formula (II) by methods known per se. For example, a compound in which $R^1$ is lower alkyl, lower alkenyl, lower alkynyl, benzyl or cyclopropylmethyl may be prepared by "N-alkylating" a compound in which $R^1$ is hydrogen. By "N-alkylating" is meant introducing onto the nitrogen atom of the hexahydroazepine ring a lower alkyl, lower alkenyl, lower alkynyl, benzyl or cyclopropylmethyl radical. In one method of carrying out the "N-alkylating" process a compound of general formula (II) in which $R^1$ is hydrogen is reacted with a halide of general formula $$R^{1\prime} - Hal$$

where $R^{1\prime}$ is lower alkyl, lower alkenyl, lower alkynyl, benzyl or cyclopropylmethyl in the presence of an acid acceptor such as an alkali metal carbonate (e.g. potassium carbonate) preferably in solution in an organic solvent. In an alternative "N-alkylating" process a 1-methyl group can be introduced by reductive methylation, for example, using formaldehyde and hydrogen in the presence of a hydrogenation catalyst. Compounds in which $R^1$ is lower alkyl can also be obtained by reduction with a hydride transfer agent (e.g. lithium aluminium hydride) of a corresponding compound in which $R^1$ is acyl.

A compound of general formula (II) in which R is a hydrogen atom can be obtained from a corresponding compound in which R is lower alkyl or benzyl by splitting off the ether group in known manner, e.g. by treating the lower alkyl or benzyl ether with hydrogen bromide or boron tribromide or by subjecting the benzyl ether to hydrogenolysis. Similarly a compound of general formula (II) in which $R^1$ is benzyl may be hydrogenolysed to a compound of general formula (II) in which $R^1$ is hydrogen which, if desired may then be "alkylated" as hereinbefore described.

A compound of general formula (II) in which R is hydrogen can be acylated (e.g. with acetic anhydride) to give a corresponding compound in which R is a lower alkanoyl radical.

The intermediate compounds of general formula (III) and their acid addition salts can be prepared by a process which comprises lower alkylating, lower alkenylating or lower alkynylating a compound of general formula (IV)

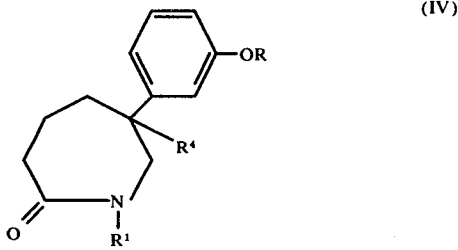

The product of a process involving lower alkylating, lower alkenylating or lower alkynylating a compound of general formula (IV) depends on the reaction conditions used. For example, if the compound of general formula (IV) in which $R^1$ is hydrogen is converted to its alkali metal salt (e.g. by reaction with sodium, sodamide or sodium hydride) and the alkali metal salt reacted with a lower alkyl, lower alkenyl, lower alkynyl or benzyl halide in an organic solvent such as benzene a compound of general formula (IV) in which $R^1$ is lower alkyl, lower alkenyl, lower alkynyl or benzyl can be isolated. However, if, for example, a compound of general formula (IV) is converted into its alkali metal salt (preferably by reaction with sodamide in liquid ammonia) and the alkali metal salt is reacted with a lower alkyl, lower alkenyl or lower alkynyl halide in liquid ammonia a compound of general formula (III) can be obtained. By choice of suitable molecular proportion of the reactants a compound of formula (III) may be obtained in which $R^2$ is hydrogen and $R^3$ is lower alkyl, lower alkenyl or lower alkynyl or both $R^2$ and $R^3$ are identical lower alkyl, lower alkenyl or lower alkynyl radicals. However, if it is desired to obtain a compound in which both $R^2$ and $R^3$ are lower alkyl, lower alkenyl or lower alkynyl radicals it is preferable to carry out a two stage process by first preparing the compound of general formula (III) in which $R^2$ is hydrogen and then converting this into its alkali metal salt and reacting the latter with further lower alkyl, lower alkenyl or lower alkynyl halide in liquid ammonia. By employing different halides in each of the stages of the two stage process it is possible to prepare a compound of formula (III) in which $R^2$ is a lower alkyl, lower alkenyl or lower alkynyl substituent which is different to the $R^3$ substituent. If in the starting material of general formula (IV) $R^1$ is hydrogen, then in the product of general formula (III) $R^1$ and $R^3$ will be identical lower alkyl, lower alkenyl or lower alkynyl groups. If the starting material contains an $R^1$ group other than hydrogen it is possible, of course, to obtain a product of general formula (III) in which the $R^1$ and $R^3$ groups are not the same. If a compound of general formula (III) is prepared in which $R^2$ is hydrogen the product is normally obtained as a mixture of epimers which may be separated by chromatography. This separation is exemplified in the Examples below in which the epimers are arbitrarily designated Epimer 'A' and Epimer 'B'.

The starting materials of general formula (IV) may be prepared by processes described in, or analogous to those described in, U.K. Specification No. 1,285,025.

Once a compound of general formula (III) has been prepared it may be converted into another compound of general formula (III) by methods known per se, for example those methods mentioned above for the conversion of one compound of general formula (II) into another compound of general formula (II).

The compounds of formula (I) are capable of forming acid addition salts with acids, and the invention also provides such salts, particularly the salts of compounds of general formula (II) with pharmaceutically acceptable acids. The salts may be isolated directly from the processes described above or prepared by dissolving the specific compound of formula (I) as its base in a suitable organic solvent, and treating it with a solution of the selected acid, in accordance with conventional procedures for preparing acid addition salts from base compounds generally. As examples of acids, there may be used any of hydrochloric, hydrobromic, tartaric, phosphoric, maleic, citric, methanesulphonic or p-toluenesulphonic acid.

The compounds of the invention possess one or more asymmetric carbon atoms and the compounds of the invention may be in the form of the pure enantiomorphs or mixtures of such enantiomorphs, such as racemates. If $R^2$ and $R^3$ are different the compounds possess two asymmetric carbon atoms and, as mentioned hereinabove, mixtures of such epimers may be separated by chromatography. Optical isomers may be prepared by resolving a racemic mixture by standard methods described in the literature. The racemate may be prepared by any of the processes outlined above. It is to be understood that the resolution may be carried out on the racemic mixture of the final desired product or it may be carried out on a racemic precursor of the desired product.

The compounds of general formula (II) exhibit pharmacological activity as analgesic agents as shown by standard tests on warm-blooded animals. The compounds are tested for analgesic activity by the radiant heat on tail method of D'Amour — Smith, J. Pharmacol, 22 74 (1941). When tested by this procedure the compounds of general formula (II) generally demonstrated analgesic activity as a dosage of between 5 and 200 mg./kg.

As the compounds of general formula (II) show pharmaceutical activity the invention further provides a pharmaceutical composition which comprises a compound of general formula (II) or a pharmaceutically acceptable acid addition salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly catchets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from 5 mg. or less to 500 mg. or more, according to the particular need and the activity of the active ingredient. The invention also includes the compounds in the absence of carrier where the compounds are in unit dosage form.

The following Examples illustrate the invention.

EXAMPLE 1

6-Ethyl-6-(m-methoxyphenyl)-1,3-dimethylhexahydro-2H-azepin-2-one, (Epimers A and B)

i. 6-Ethyl-6-(m-methoxyphenyl)hexahydro-2H-azepin-2-one (19.6 g) in dry benzene (200 ml.) was added dropwise to a stirred refluxing suspension of sodium hydride (60% suspension in oil; 4.0 g.) in dry benzene (200 ml.) under nitrogen. After the addition had been completed the reaction mixture was heated under reflux for 4 hours and then cooled to 40° C. Methyl iodide (20 ml.) was then added and the mixture stirred and heated at 40°–55° C overnight After cooling, the reaction mixture was washed with water, dried over magnesium sulphate and evaporated to an orange oil which was crystallised. The product was recrystallised from light petroleum (b.p. 80°–100° C) to give 6-ethyl-6-(m-methoxyphenyl)-1-methylhexahydro 2H-azepin-2-one (19.1 g) as colourless crystals, m.p. 69°–71° C. (Found: C, 73.2; H, 8.9; N, 5.4%. $C_{16}H_{23}NO_2$ requires: C, 73.5; H, 8.9; N, 5.4%)

ii. 6-Ethyl-6-(m-methoxyphenyl)-1-methylhexahydro-2H-azepin-2-one (15.7 g., 0.06 mole) in dry tetrahydrofuran (300 ml.) was added dropwise to a suspension of sodium amide (2.7 g., 0.068 mole) in liquid ammonia (400 ml.). After stirring for 1 hour methyl iodide (8 g., 0.07 mole) was added and after stirring for a further hour another portion of methyl iodide (1 ml.) was added. The reaction was stirred overnight allowing the ammonia to evaporate. The tetrahydrofuran was removed under reduced pressure and ether added The solution was washed with water and dilute hydrochloric acid. After drying over magnesium sulphate, solvent was removed to leave an oil (12.5 g.) which was chromatographed on Florosil (a synthetic magnesium silica gel) eluting with a mixture of ethyl acetatebenzene (1:4). The separation by the column was followed by g.l.c. using a 2m. column of 2.5% OV 17 (a mixture of 50% phenyl and 50% methyl silicone gum) on Chromosorb A (a g.l.c. support material).

a. The first fractions contained 2.9 g. of Epimer 'B' of the title compound.

b. The middle fractions contained 3.5 g. of a mixture of Epimers 'A' and 'B' of the title compound.

c. The final fractions contained 3.5 g. of Epimer 'A' of the title compound.

EXAMPLE 2

3-Ethyl-3-(m-methoxyphenyl)-1,6-dimethylhexahydro-1H-azepine. (Epimer 'A')

Epimer 'A' of 6-ethyl-6-(m-methoxyphenyl)-1,3-dimethylhexahydro-2H-azepin-2-one [Example 1 (ii) (c); 4.4 g.] in dry ether (30 ml.) was added dropwise to a stirred suspension of lithium aluminium hydride (2 g.) in ether (20 ml.). The reaction was heated under reflux overnight, cooled, then decomposed by the addition of water (2 ml. 5N sodium hydroxide solution (2 ml.) followed by water (4 ml.). The solids formed were filtered off and, after evaporation the filtrate left a colourless oil (4.6 g.). Treatment with isopropyl alcohol and 50% aqueous hydrobromic acid gave the title compound as its hydrogen bromide salt, m.p. 160°–162° C. (Found: C, 59.3; H, 8.4; N, 3.8%. $C_{17}H_{27}NO$ HBr requires: C, 59.6; H, 8.25; N, 4.1%).

EXAMPLE 3

3-Ethyl-3-(m-methoxyphenyl)-1,6-dimethylhexahydro-1H-azepine. (Epimer B)

Epimer 'B' of 6-ethyl-6-(m-methoxyphenyl)-1,3-dimethylhexahydro-2H-azepin-2-one [Example 1 (ii) (a); 2.8 g.] in dry ether (20 ml.) was reduced with lithium aluminium hydride (1 g.) according to the procedure of Example 2. After work up, the colourless oil was distilled affording the title compound (2.39 g.), b.p. 106°–110° C. 0.1mm.

(Found: C, 78.4; H, 10.4; N, 5.3%. $C_{17}H_{27}NO$ requires: C, 78.1; H, 10.4; N, 5.4%).

EXAMPLE 4

6-Ethyl-6-(m-methoxyphenyl)-1,3,3dimethylhexahydro 2H-azepin-2-one.

The mixture of monomethylated epimers as prepared in Example 1 (ii) (b) (8.3 g.) in dry tetrahydrofuran (50 ml.) was added dropwise to a suspension of sodium amide (1.76 g.) in liquid ammonia (250 ml.). The reaction was stirred for 1 hour and methyl iodide (3.7 ml.) added. Dry ether (200 ml.) was added and the mixture stirred over night allowing the ammonia to evaporate off. The reaction mixture was washed with water and dilute hydrochloric acid, dried over magnesium sulphate and evaporated to a colourless oil which was distilled to give the title compound (7.2 g.), b.p. 164°–166° C 0.1mm. G.l.c. showed that the product was >90% pure.

EXAMPLE 5

3-Ethyl-3-(m-methoxyphenyl)-1,6-trimethylhexahydro-1H-azepine

The lactam prepared in Example 4 (2.55 g.) was reduced with lithium aluminium hydride (0.8 g.) according to the procedures of Examples 2 and 3. The title compound was obtained as a colourless oil (1.82 g.), b.p. 100°–102° C 0.10mm.

EXAMPLE 6 m-(3-Ethyl-1,6-dimethylhexahydro-1H-azepin-3-yl)phenol hydrobromide (Epimer 'A')

The product from Example 2 (3.8 g.) was heated under reflux with 48% hydrobromic acid (25 ml.) for 1.5 hr. The solvent was removed under reduced pressure, and the viscous oil re-evaporated several times from isopropanol. Dilution with ether gave the title compound (3.3 g.) m.p. 224°–6° C. (Found: C, 58.5; H, 8.1; N, 4.1% $C_{16}H_{25}NO$ HBr requires: C; 58.5; H, 8.0; N, 4.3%).

EXAMPLE 7 m-(3-Ethyl-1,6-dimethylhexahydro-1H-azepin-3-yl)phenol hydrobromide (Epimer 'B')

The distilled oil from Example 3 (1.1 g.) was heated under reflux with 48% hydrobromic acid (10 ml.) for 2 hours. The product was isolated by a procedure analogous to that described in Example 6 to give the title compound (1.07 g.), m.p. 210°–211° C. (Found: C, 58.35; H, 8.0; N, 4.2% $C_{16}H_{25}NO$ HBr requires: C, 58.5; H, 8.0; N, 4.3%).

EXAMPLE 8 m-(3-Ethyl-1,6,6-trimethylhexahydro-1H-azepin-3-yl)phenol

The azepine from Example 5 (1.75 g.) was heated under reflux with 48% hydrobromic acid (15 ml.) for 1.5 hr. After working up by a procedure analogous to that described in Example 6, the product was obtained as its hydrogen bromide salt (1.43 g.), m.p. 211°–212° C. (Found: C, 59.8; H, 8.5; N, 4.0%. $C_{17}H_{27}NO$ HBr requires: C, 59.6; H, 8.25; N, 4.1%).

I claim:

1. A compound selected from the group consisting of a hexahydroazepine of formula

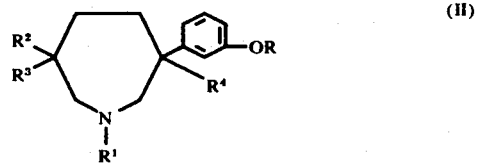

(II)

and an acid addition salt thereof with a pharmaceutically acceptable acid wherein R represents hydrogen, lower alkyl, benzyl or lower alkanoyl, $R^1$ represents hydrogen, lower alkyl, lower alkenyl, lower alkynyl, benzyl or cyclopropylmethyl, $R^2$ represents hydrogen, lower alkyl, lower alkenyl or lower alkynyl, $R^3$ represents lower alkyl, lower alkenyl or lower alkynyl and $R^4$ represents lower alkyl.

2. A compound as claimed in claim 1 which is 3-ethyl-3-(m-methoxyphenyl)-1,6-dimethylhexahydro-1H-azepine.

3. A compound as claimed in claim 1 which is 3-ethyl-3-(m-methoxyphenyl)-1,6,6-trimethylhexahydro-1H-azepine.

4. A compound as claimed in claim 1 which is m-(3-ethyl-1,6-dimethylhexahydro-1H-azepin-3-yl)phenol.

5. A compound as claimed in claim 1 which is m-(3-ethyl-1,6,6-trimethylhexahydro-1H-azepin-3-yl)phenol.

* * * * *